United States Patent
Wu et al.

(10) Patent No.: US 7,358,199 B2
(45) Date of Patent: Apr. 15, 2008

(54) METHOD OF FABRICATING SEMICONDUCTOR INTEGRATED CIRCUITS

(75) Inventors: I-Wen Wu, Taoyuan County (TW); Chen-Chiu Tseng, Hsin-Chu Hsien (TW)

(73) Assignee: United Microelectronics Corp., Hsin-Chu (TW)

( * ) Notice: Subject to any disclaimer, the term of this patent is extended or adjusted under 35 U.S.C. 154(b) by 331 days.

(21) Appl. No.: 11/160,107

(22) Filed: Jun. 9, 2005

(65) Prior Publication Data

US 2006/0281335 A1 Dec. 14, 2006

(51) Int. Cl.
*H01L 21/47* (2006.01)
*H01L 21/312* (2006.01)
*B05D 5/12* (2006.01)
*B05D 3/12* (2006.01)

(52) U.S. Cl. ............. 438/782; 427/9; 427/10; 427/240; 438/780

(58) Field of Classification Search ............... 438/14, 438/780, 782; 427/8, 9, 10, 240, 96.2
See application file for complete search history.

(56) References Cited

U.S. PATENT DOCUMENTS

| | | | |
|---|---|---|---|
| 4,851,311 A * | 7/1989 | Millis et al. ............ 430/30 |
| 4,948,259 A * | 8/1990 | Enke et al. ............ 356/632 |
| 5,196,353 A * | 3/1993 | Sandhu et al. ........... 438/5 |
| 5,242,524 A * | 9/1993 | Leach et al. ......... 156/345.13 |
| 5,308,438 A * | 5/1994 | Cote et al. ............ 216/86 |
| 5,413,941 A * | 5/1995 | Koos et al. ............ 438/16 |
| 5,919,520 A * | 7/1999 | Tateyama et al. ....... 427/240 |
| 5,949,927 A * | 9/1999 | Tang ................. 385/12 |
| 6,340,644 B1 * | 1/2002 | Becker et al. .......... 438/782 |
| 6,462,817 B1 * | 10/2002 | Strocchia-Rivera ...... 356/369 |
| 6,485,782 B2 * | 11/2002 | Takamori ............. 427/240 |
| 6,507,394 B1 | 1/2003 | Cheng et al. |
| 6,512,735 B1 * | 1/2003 | Takeda et al. ........ 369/275.4 |
| 6,558,964 B2 * | 5/2003 | Treur ................ 438/14 |
| 6,875,640 B1 * | 4/2005 | Farnworth et al. ...... 438/127 |
| 6,957,154 B2 * | 10/2005 | Steele et al. .......... 702/35 |
| 2001/0022897 A1 * | 9/2001 | Ogata et al. .......... 396/564 |
| 2002/0093648 A1 * | 7/2002 | Nikoonahad et al. .... 356/237.1 |
| 2002/0102749 A1 * | 8/2002 | Fielden et al. ......... 438/14 |
| 2003/0147060 A1 * | 8/2003 | Tokuda et al. ......... 355/53 |
| 2004/0221954 A1 | 11/2004 | Takizawa |
| 2005/0158653 A1 * | 7/2005 | Hatakeyama et al. ... 430/270.1 |

(Continued)

FOREIGN PATENT DOCUMENTS

CN 1539560 A 10/2004

(Continued)

*Primary Examiner*—M. Wilczewski
(74) *Attorney, Agent, or Firm*—Winston Hsu

(57) ABSTRACT

A method of fabricating semiconductor integrated circuits includes (1) providing a spin-on tool comprising a rotatable platen for holding and spinning a wafer disposed thereon, a fluid supply system for providing spin-on solution onto the wafer, and a detector fixed in a position above the wafer, wherein the wafer has a radius R; (2) spin-on coating the wafer by depositing the spin-on solution onto surface of the wafer from its center and spinning-off to leave a spin coat material layer; and (3) spinning the wafer and scanning the spin coat material layer by impinging an incident light beam emanated from the fixed detector and detecting a reflected light beam.

7 Claims, 2 Drawing Sheets

U.S. PATENT DOCUMENTS

| | | | |
|---|---|---|---|
| 2005/0206893 A1* | 9/2005 | Montagu | 356/317 |
| 2006/0072807 A1* | 4/2006 | Bultman et al. | 382/149 |
| 2006/0151111 A1* | 7/2006 | Tang | 156/345.13 |
| 2006/0281335 A1* | 12/2006 | Wu et al. | 438/782 |

FOREIGN PATENT DOCUMENTS

TW 519710 2/2003

* cited by examiner

METHOD OF FABRICATING SEMICONDUCTOR INTEGRATED CIRCUITS

BACKGROUND OF INVENTION

1. Field of the Invention

The present invention relates generally to the fabrication of semiconductor integrated circuits and, more particularly, to a method of fabricating semiconductor integrated circuits with improved yields.

2. Description of the Prior Art

The manufacture of integrated circuits requires high cost equipments, clean rooms and cutting edge process technologies. To amortize this high capital expenditure, it is necessary to increase the yields as much as possible, but with costs for quality control and process realization at an acceptable level.

Spin-on coated materials such as photoresists, spin-on glasses and some low-k materials are frequently used in this art. The spin-on material such as photoresist is dispensed onto a spinning wafer from its center. Particles deposited on the wafer surface usually result in sectorial defect areas on the wafer, which are typically inspected by visual means. For example, an operator places the wafer under a microscope and inspects the wafer surface to identify the defect areas. Such manual process is done off-line, and is thus time consuming.

U.S. Pat. No. 6,507,394 discloses a method of inspecting the surface of a semiconductor device. The disclosed optical inspection system for detecting defects on the surface of a semiconductor wafer requires two light sources and two light receivers mounted as a common assembly, which is rotated such that two curtains of light and corresponding linear photosensor arrays circularly scan the wafer surface. The reflected light is analyzed to determine the presence of surface defects. Marks applied to the wafer surface provide amplitude and timing references used to adjust and synchronize the analyzed signals.

It is disadvantageous that according to this patent the wafer has to be removed from the wafer stage of a spin coat system and then placed on a conveyor driven by rollers, which moves the wafer linearly. A motor is also required to rotate the sensor assembly. Besides, such inspection system is complicated and is not particularly effective in detecting the above-mentioned sectorial defect areas on the wafer.

SUMMARY OF INVENTION

It is therefore an object of the present invention to provide a simplified and more effective method for detecting the aforesaid sectorial defect areas particularly produced in the spin coat processes, thereby promoting production yields.

In accordance with one preferred embodiment of this invention, a method of fabricating semiconductor integrated circuits includes:

(1) providing a spin-on tool comprising a rotatable platen for holding and spinning a wafer disposed thereon, a fluid supply system for providing spin-on solution onto the wafer, and a detector fixed in a position above the wafer, wherein the wafer has a radius R;

(2) spin-on coating the wafer by depositing the spin-on solution onto surface of the wafer from its center and spinning-off to leave a spin coat material layer; and (3) spinning the wafer and scanning the spin coat material layer by impinging an incident light beam emanated from the fixed detector and detecting a reflected light beam.

These and other objectives of the present invention will no doubt become obvious to those of ordinary skill in the art after reading the following detailed description of the preferred embodiment that is illustrated in the various figures and drawings.

BRIEF DESCRIPTION OF DRAWINGS

The accompanying drawings are included to provide a further understanding of the invention, and are incorporated in and constitute a part of this specification. The drawings illustrate embodiments of the invention and, together with the description, serve to explain the principles of the invention. In the drawings.

DETAILED DESCRIPTION

The present invention pertains to the non-contact measurement of film surface uniformity of a wafer, and is suited for any kinds of spin-on applications such as, for example, photoresist coatings, bottom/top anti-reflection coatings, spin-on glass, and low-k materials. It is essential to maintain the uniformity of a resist film's surface during or after the photoresist spin coating process since the uniformity of a resist film's surface can adversely affect pattern transfer accuracy in the subsequent exposure stage. As stated supra, particles deposited on the wafer surface usually result in sectorial defect areas on the wafer, which are typically inspected by visual means.

Figure 1:
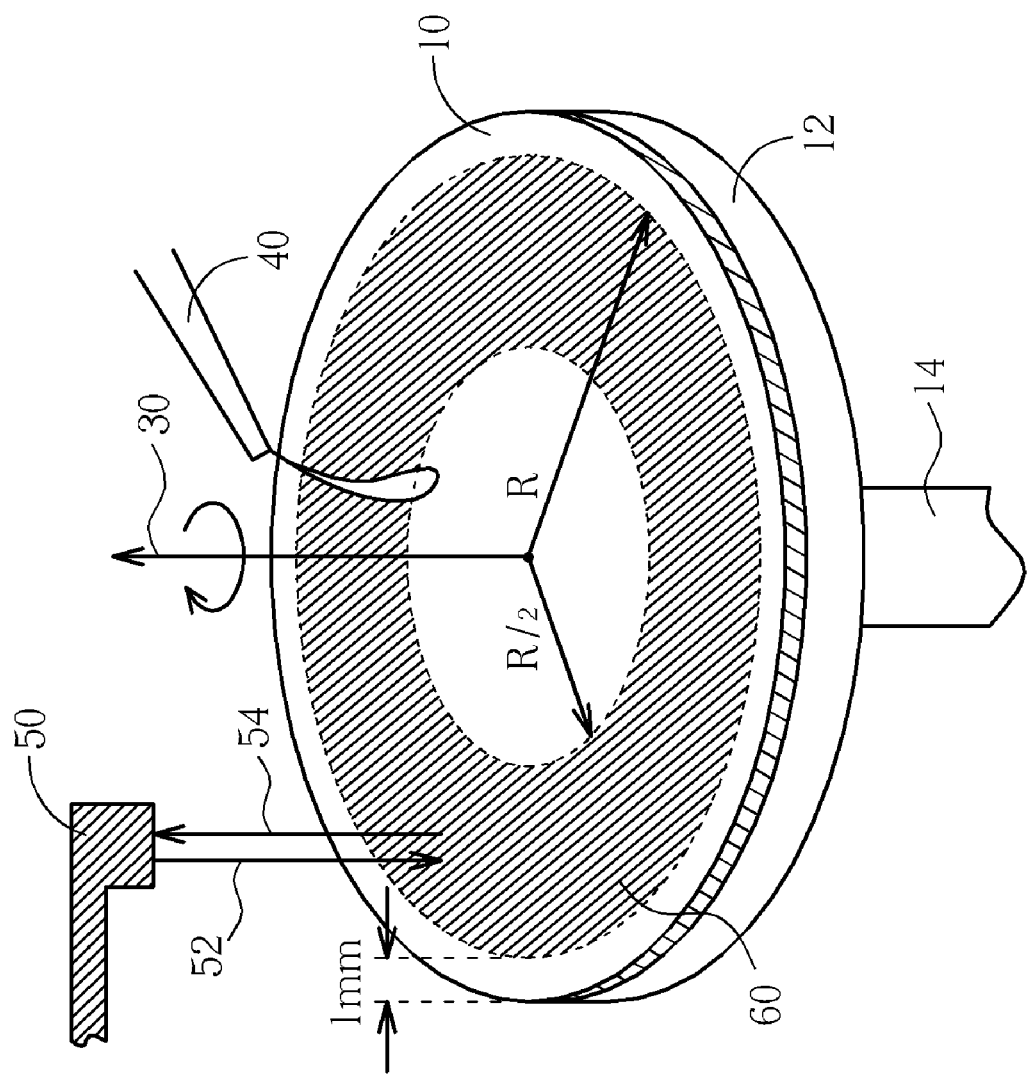
FIG. 1 is a schematic diagram showing one preferred embodiment of the present invention.

Referring to FIG. 1, a schematic diagram showing one preferred embodiment of the present invention is depicted. A wafer 10 with a radius R is disposed on a platen 12 of a spin-coating tool. The wafer 10 and the platen 12 driven by a shaft 14 together rotate about an axis 30. In some cases, the platen 12 may be a vacuum chuck. Spin-on coating solution such as photoresist is provided to the wafer surface by a fluid supply system 40 that is situated above the platen 12. Such coating solution is deposited onto the surface of the wafer 10 from its center and spun-off to leave a uniform layer (not explicitly shown in FIG. 1). The method may further comprise a step of baking the spin coat material layer prior to scanning the spin coat material layer.

A fixed detector 50 is situated above the wafer 10. According to the preferred embodiment of this invention, the detector 50 is an optical detector. In other cases, non-optical detectors such as capacitance-based or ultrasonic detectors may be used. In accordance with the preferred embodiment, an incident light beam 52 emanated from the detector 50 impinges on the wafer surface that is coated by a layer of spin-on material. The reflected light beam 54 is detected by the detector 50. To effectively detect the sectorial defect areas on the wafer, it is suggested that the incident light beam 52 impinge within the belt area 60 (specifically indicated by darker pattern) from radius R/2 to the perimeter that is about 1 millimeter from the wafer rim. The distal area between the wafer rim and the perimeter that is 1 millimeter from the wafer rim is deemed not applicable because the signal noise is high in this area. According to this embodiment, the light intensity is lower than the threshold exposure energy of the photoresist film that is coated on the wafer 10.

Figure 2:
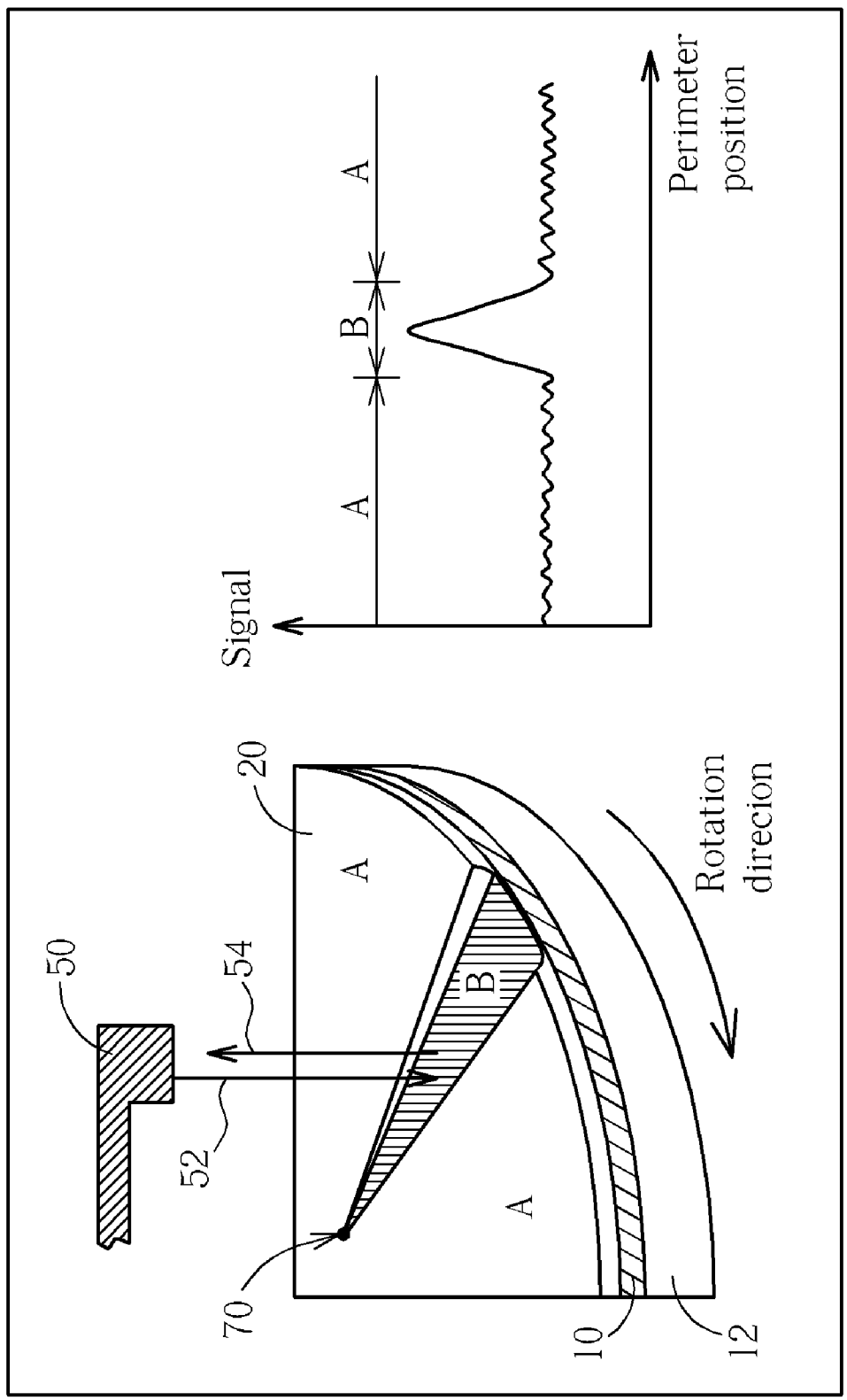
FIG. 2 demonstrates at left a perspective view of an enlarged portion of the wafer including a sectorial defect area in the photoresist coated on the wafer, and at right a plot of the detected light signal.

Referring to FIG. 2, a perspective view of an enlarged portion of the wafer including a sectorial defect area in the photoresist coated on the wafer 10, and a plot of the detected light signal are illustrated. As shown in FIG. 2, a photoresist film 20 is spin-coated on the wafer 10 that is positioned on the platen 12. The photoresist film 20 may cover a material layer that is to be patterned in subsequent stage, for example, a metal layer. The photoresist film 20 may further combined with an anit-reflection coating at its bottom (known as "BARC") or top (known as "TARC). The top surface of the photoresist film 20 is divided into two areas: Areas A and B, wherein Area A represents a flat surface and Area B represents a sectorial defect area caused by particle 70. The film thickness of the photoresist film 20 within Area B is thinner than that within Area A. In a worse case, the underlying layer may be exposed.

Still referring to FIG. 2, as the fixed detector 50 scans the wafer surface in the direction that is opposite to the wafer rotation direction, the intensities of the reflected light beam 54 are measured. The schematic signal plot detected by the detector 50 is demonstrated at right. A peak is detected corresponding to Area B. According to this embodiment, once a peak having a peak width at half height that is larger than 1 angle degree is detected, the wafer 10 is reworked. It is advantageous to use this invention because the detection system is inexpensive and is effective in detecting defect areas on the wafer. Further, the surface inspection may be executed on the spin-on tool right after spin-on process without the need of removing the wafer from the platen, and thus promotes throughput.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. A method of fabricating semiconductor integrated circuits comprising:

providing a spin-on tool comprising a rotatable platen for holding and spinning a wafer disposed thereon, a fluid supply system for providing spin-on solution onto said wafer, and a detector fixed in a position above said wafer, wherein said wafer has a radius R;

spin-on coating said wafer by depositing said spin-on solution onto surface of said wafer from its center and spinning-off to leave a spin coat material layer; and spinning said wafer and scanning said spin coat material layer by impinging an incident light beam emanated from said fixed detector and detecting a reflected light beam.

2. The method according to claim 1 wherein said incident light beam impinges within a belt area ranging from radius R/2 to a perimeter that is about 1 millimeter from said wafer's rim.

3. The method according to claim 1 wherein said spin-on solution comprises photoresist.

4. The method according to claim 1 wherein said spin coat material layer comprises an anti-reflection coating.

5. The method according to claim 1 further comprising a step of baking said spin coat material layer prior to the step of scanning said spin coat material layer.

6. The method according to claim 1 wherein said spin coat material layer is a photoresist layer and said incident light beam has a light intensity that is lower than a threshold exposure energy of said photoresist layer.

7. A method of fabricating semiconductor integrated circuits comprising:

providing a spin-on tool comprising a rotatable platen for holding and spinning a wafer disposed thereon, a fluid supply system for providing spin-on solution onto said wafer, and a detector fixed in a position above said wafer, wherein said wafer has a radius R;

spin-on coating said wafer by depositing said spin-on solution onto surface of said wafer from its center and spinning-off to leave a spin coat material layer; and spinning said wafer and assessing surface uniformity of said spin coat material layer by scanning said spin coat material layer using said fixed detector.

* * * * *